(12) United States Patent
Crowther et al.

(10) Patent No.: US 6,339,134 B1
(45) Date of Patent: Jan. 15, 2002

(54) POLYMERIZATION PROCESS FOR PRODUCING EASIER PROCESSING POLYMERS

(75) Inventors: Donna J. Crowther, Baytown; Ching-Tai Lue, Houston, both of TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/306,142

(22) Filed: May 6, 1999

(51) Int. Cl.$^7$ ................................ C08F 4/16; C08F 10/02
(52) U.S. Cl. .................. 526/128; 526/160; 526/352; 526/348; 526/943; 526/901; 502/152; 556/53
(58) Field of Search ............................. 526/160, 128, 526/948, 351, 352, 901, 348, 943; 556/53; 502/102, 152

(56) References Cited

U.S. PATENT DOCUMENTS

| | | | |
|---|---|---|---|
| 5,281,679 A | 1/1994 | Jejelowo et al. | 526/114 |
| 5,350,817 A | 9/1994 | Winter et al. | 526/119 |
| 5,439,994 A | 8/1995 | Inoue et al. | 526/114 |
| 5,451,649 A | 9/1995 | Zenk et al. | 526/160 |
| 5,470,811 A | 11/1995 | Jejelowo et al. | 502/117 |
| 5,534,473 A | 7/1996 | Welch et al. | 502/117 |
| 5,539,056 A | 7/1996 | Yang et al. | 525/240 |
| 5,571,880 A | 11/1996 | Alt et al. | 526/160 |
| 5,594,078 A | 1/1997 | Welch et al. | 526/119 |
| 5,627,247 A | 5/1997 | Alt et al. | 526/160 |
| 5,668,230 A | 9/1997 | Schertl et al. | 526/160 |
| 5,714,427 A | 2/1998 | Winter et al. | 502/117 |
| 5,798,427 A | 8/1998 | Foster et al. | 526/352 |

FOREIGN PATENT DOCUMENTS

| | | |
|---|---|---|
| EP | 0 316 155 A2 | 5/1989 |
| EP | 0399348 B1 and A3 | 11/1990 |
| EP | 0524624 A1 and A3 | 1/1993 |
| EP | 0662267 A2 and A3 | 8/1995 |
| EP | 0672675 A1 | 9/1995 |
| EP | 0316155 B1 | 2/1996 |
| EP | 0516018 B1 | 3/1996 |
| EP | 0705851 A2 and A3 | 4/1996 |
| EP | 0700937 A2 and A3 | 2/1997 |
| EP | 0780396 A1 | 6/1997 |
| EP | 0528041 B1 | 11/1997 |
| EP | 0 846 696 * | 6/1998 |
| EP | 0955305 A1 | 11/1999 |
| EP | 0 955 305 A1 | 11/1999 |
| WO | WO 92/00333 | 1/1992 |

OTHER PUBLICATIONS

Chien et al., (1,3–Propanediyl)silylene–bis(1–indenyl)dichlorozirconium. Synthesis and polymerization catalysis JOMC 487 (1995) 29–34.*
Chien et al., Silolene–Bridged Zirconocenium Polymerization Catalysts. Journal of Polymer Science, Part A: Polymer Chemistry, vol. 32, 149–158, 1994.*
Brenner v. Ladd, Commr. Patents, 147 USPQ 87, (DC DC 1965).*
Angew. Chem. Int. Ed., Leclerc et al., 1998, 37, No. 7.
Metallocenes make copolymers alternate, Wilson, C&EN, May 4, 1998.
Macromol. Rapid Commun., Uozumi et al., 18, 883–889 (1997).
J. of Polymer Science, Part A: Polymer Chemistry, Tsai et al., vol. 32, 149–158 (1994).

* cited by examiner

Primary Examiner—David W. Wu
Assistant Examiner—R. Harlan
(74) Attorney, Agent, or Firm—Jaimes Sher; Lisa Kimes Jones

(57) ABSTRACT

The present invention relates to a process for polymerizing olefin(s) utilizing a cyclic bridged metallocene-type catalyst system to produce enhanced processability polymers.

24 Claims, No Drawings

POLYMERIZATION PROCESS FOR PRODUCING EASIER PROCESSING POLYMERS

FIELD OF THE INVENTION

The present invention relates to a process for polymerizing olefin(s) to produce polymers having improved processability. Also, the invention is directed to a bulky ligand metallocene-type catalyst compound and catalyst system for use in the polymerization of olefin(s) to produce polymers that are easier to process into various articles of manufacture. In particular, the invention is directed to cyclic bridged bulky ligand metallocene-type catalyst systems, their use in a polymerization process, and products produced therefrom.

BACKGROUND OF THE INVENTION

Processability is the ability to economically process and shape a polymer uniformly. Processability involves such elements as how easily the polymer flows, melt strength, and whether or not the extrudate is distortion free. Typical bulky ligand metallocene-type catalyzed polyethylenes (mPE) are somewhat more difficult to process than low density polyethylenes (LDPE) made in a high pressure polymerization process. Generally, mPE's require more motor power and produce higher extruder pressures to match the extrusion rate of LDPE's. Typical mPE's also have lower melt strength which, for example, adversely affects bubble stability during blown film extrusion, and they are prone to melt fracture at commercial shear rates. On the other hand, however, mPE's exhibit superior physical properties as compared to LDPE's.

It is now common practice in the industry to add various levels of an LDPE to an mPE to increase melt strength, to increase shear sensitivity, i.e., to increase flow at commercial shear rates; and to reduce the tendency to melt fracture. However, these blends generally have poor mechanical properties as compared with neat mPE.

Traditionally, metallocene catalysts produce polymers having a narrow molecular weight distribution. Narrow molecular weight distribution polymers tend to be more difficult to process. The broader the polymer molecular weight distribution the easier the polymer is to process. A technique to improve the processability of mPE's is to broaden the products' molecular weight distribution (MWD) by blending two or more mPE's with significantly different molecular weights, or by changing to a polymerization catalyst or mixture of catalysts that produce broad MWD polymers.

In the art specific bulky ligand metallocene-type catalyst compound characteristics have been shown to produce polymers that are easier to process. For example, U.S. Pat. No. 5,281,679 discusses bulky ligand metallocene-type catalyst compounds where the bulky ligand is substituted with a substituent having a secondary or tertiary carbon atom for the producing of broader molecular weight distribution polymers. U.S. Pat. No. 5,470,811 describes the use of a mixture of bulky ligand metallocene-type catalysts for producing easy processing polymers. Also, U.S. Pat. No. 5,798,427 addresses the production of polymers having enhanced processability using a bulky ligand metallocene-type catalyst compound where the bulky ligands are specifically substituted indenyl ligands.

A need exists in the industry for a process using a bulky ligand metallocene-type catalyst to produce more easily processable polymers.

SUMMARY OF THE INVENTION

This invention relates to a polymerization process utilizing a bridged bulky ligand metallocene-type catalyst system for producing polymer products that have excellent processability and enhanced physical properties. Also, the invention is directed to improved bridged bulky ligand metallocene-type catalyst compounds having a cyclic bridge, catalyst systems comprising these compounds, and polymerizing processes utilizing these compounds.

The preferred polymerization processes are a gas phase or a slurry phase process, most preferably a gas phase process.

In an embodiment, the invention provides for a process for polymerizing ethylene alone or in combination with one or more other olefin(s) in the presence of a cyclic bridged metallocene-type catalyst compound, preferably an achiral cyclic bridged metallocene-type catalyst compound, even more preferably an achiral cyclic bridged metallocene-type catalyst compound having two substituted bulky ligands and an activator. In a most preferred embodiment, the cyclic bridged metallocene-type catalyst compound has two bulky ligands only one of which is a substituted bulky ligand.

In another embodiment, the invention relates to a gas phase or slurry phase process for polymerizing olefin(s) using a cyclic bridged metallocene-type catalyst system to produce a polymer product having a $M_z/M_w$ greater than or equal to 3 and an $I_{21}/I_2$ of greater than 35. In this embodiment, it is particularly preferred that a supported cyclic bridged metallocene-type catalyst system is used.

DETAILED DESCRIPTION OF THE INVENTION

Introduction

The invention relates to a polymerization process for producing easy processing polymers using a cyclic bridged bulky ligand metallocene-type catalyst system. It has been suprisingly discovered that using the cyclic bridged metallocene-type catalysts of the invention, particularly in a slurry or gas phase polymerization process, produces polymers that have a high Melt Index Ratio (MIR). MIR is simply the ratio of $I_{21}/I_2$, where $I_{21}$ is measured by ASTM-D-1238-F and $I_2$ known as Melt Index (MI) is measured by ASTM-D-1238-E.

Bulky Ligand Metallocene-Type Catalyst Compounds

Generally, bulky ligand metallocene-type catalyst compounds include half and full sandwich compounds having one or more bulky ligands bonded to at least one metal atom. Typical bulky ligand metallocene-type compounds are generally described as containing one or more bulky ligand(s) and one or more leaving group(s) bonded to at least one metal atom. In one preferred embodiment, at least one bulky ligand is η-bonded to a metal atom, most preferably $\eta^5$-bonded to the metal atom.

The bulky ligands are generally represented by one or more open, acyclic, or fused ring(s) or ring system(s) or a combination thereof. These bulky ligands, preferably ring(s) or ring system(s) are typically composed of atoms selected from Groups 13 to 16 atoms of the Periodic Table of Elements, preferably the atoms are selected from the group consisting of carbon, nitrogen, oxygen, silicon, sulfur, phosphorous, boron and aluminum or a combination thereof. Most preferably the ring(s) or ring system(s) are composed of carbon atoms such as but not limited to those cyclopentadienyl ligands or cyclopentadienyl-type ligand structures or other similar functioning ligand structure such as a pentadiene, a cyclooctatetraendiyl or an imide ligand. The metal atom is preferably selected from Groups 3 through 15 and the lanthanide or actinide series of the Periodic Table of Elements. Preferably the metal is a transition metal from Groups 4 through 12, more preferably 4, 5 and 6, and most preferably the metal is from Group 4.

In one embodiment, the bulky ligand metallocene-type catalyst compounds of the invention are represented by the formula:

$$L^A L^B M Q_n \quad (I)$$

where M is a metal atom from the Periodic Table of the Elements and may be a Group 3 to 12 metal or from the lanthanide or actinide series of the Periodic Table of Elements, preferably M is a Group 4, 5 or 6 transition metal, more preferably M is a Group 4 transition metal, even more preferably M is zirconium, hafnium or titanium. The bulky ligands, $L^A$ and $L^B$, are open, acyclic, or fused ring(s) or ring system(s) such as unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, indenyl ligands, benzindenyl ligands, fluorenyl ligands, octahydrofluorenyl ligands, cyclooctatetraendiyl ligands, azenyl ligands, azulene ligands, pentalene ligands, phosphoyl ligands, pyrrolyl ligands, pyrozolyl ligands, carbazolyl ligands, borabenzene ligands and the like, including hydrogenated versions thereof, for example tetrahydroindenyl ligands. In one embodiment, $L^A$ and $L^B$ may be any other ligand structure capable of $\eta$-bonding to M, preferably $\eta^3$-bonding to M, and most preferably $\eta^5$-bonding to M. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. For the purposes of this patent specification and appended claims the term "leaving group" is any ligand that can be abstracted from a bulky ligand metallocene-type catalyst compound to form a bulky ligand metallocene-type catalyst cation capable of polymerizing one or more olefin(s). In one embodiment, Q is a monoanionic labile ligand having a sigma-bond to M. Depending on the oxidation state of the metal, the value for n is 0, 1 or 2 such that formula (I) above represents a neutral bulky ligand metallocene-type catalyst compound. Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methyoxy, ethyoxy, propoxy, phenoxy, bis(N-methylanilide), dimethylamide, dimethylphosphide radicals and the like.

The bridged bulky ligand metallocene-type catalyst compounds of the invention include those of formula (I) where $L^A$ and $L^B$ are bridged to each other by a cyclic bridging group, A. For the purposes of this patent application and appended claims, the cyclic bridging group A comprises greater than 3 non-hydrogen atoms, preferably greater than 3 carbon atoms forming a ring or ring system about at least one other Group 13 to 16 atom. Non-limiting examples of Group 13 to 16 atoms include at least one of a carbon, oxygen, nitrogen, silicon, boron, germanium and tin atom or a combination thereof. In a preferred embodiment, the cyclic bridging group A contains a carbon, silicon or germanium atom, most preferably A contains at least one silicon atom. The atoms forming the ring system of A may be substituted with substituents as defined above for R.

Non-limiting examples of cyclic bridging groups A include cyclo-tri or tetra-alkylene silyl or include cyclo-tri or tetra-alkylene germyl groups, for example, cyclotrimethylenesilyl group or cyclotetramethylenesilyl group.

Other examples of cyclic bridging groups are represented by the following structures:

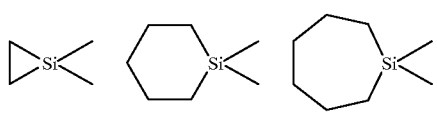

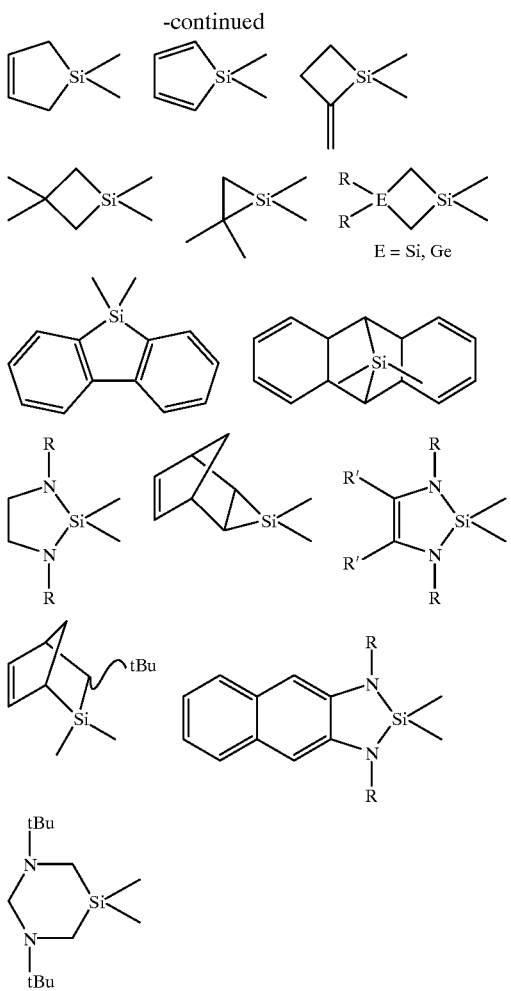

In a preferred embodiment, the bulky ligand metallocene-type catalyst compounds of the invention include cyclotrimethylenesilyl(tetramethyl cyclopentadienyl)(cyclopentadienyl)zirconium dichloride, cyclotetramethylenesilyl(tetramethyl cyclopentadienyl)(cyclopentadienyl) zirconium dichloride, cyclotrimethylenesilyl (tetramethyl cyclopentadienyl) (2-methyl indenyl) zirconium dichloride, cyclotrimethylenesilyl(tetramethyl cyclopentadienyl)(3-methyl cyclopentadienyl)zirconium dichloride, cyclotrimethylenesilyl bis(2-methyl indenyl) zirconium dichloride, cyclotrimethylenesilyl(tetramethyl cyclopentadienyl)(2,3,5-trimethyl cyclopentadienyl) zirconium dichloride, and cyclotrimethylenesilyl bis(tetra methyl cyclopentadienyl)zirconium dichloride.

In another embodiment, the bulky ligand metallocene-type catalyst compound of the invention is represented by the formula:

$$(C_5H_{4-d}R_d)(R'A_xR')(C_5H_{4-d}R_d)M\ Q_{g-2} \qquad (II)$$

where M is a Group 4, 5, 6 transition metal, $(C_5H_{4-d}R_d)$ is an unsubstituted or substituted, cyclopentadienyl ligand or cyclopentadienyl-type bulky ligand bonded to M, each R, which can be the same or different, is hydrogen or a substituent group containing up to 50 non-hydrogen atoms or substituted or unsubstituted hydrocarbyl having from 1 to 30 carbon atoms or combinations thereof, or two or more carbon atoms are joined together to form a part of a substituted or unsubstituted ring or ring system having 4 to 30 carbon atoms, $R'A_xR'$ is a cyclic bridging group, where A is one or more of, or a combination of carbon, germanium, silicon, tin, phosphorous or bridging two $(C_5H_{4-d}R_d)$ rings, and the two R''s form a cyclic ring or ring system with A; more particularly, non-limiting examples of cyclic bridging group A may be represented by $R'_2C$, $R'_2Si$, $R'_2Ge$ and $R'P$, where the two R''s are joined to form a ring or ring system. In one embodiment, R' is a hydrocarbyl containing a heteroatom, for example boron, nitrogen, oxygen or a combination thereof. The two R''s may be independently, hydrocarbyl, substituted hydrocarbyl, halocarbyl, substituted halocarbyl, hydrocarbyl-substituted organometalloid, halocarbyl-substituted organometalloid, where the two R''s may be joined to form a ring or ring system having from 2 to 100 non-hydrogen atoms, preferably from 3 to 50 carbon atoms; and independently, each Q can be the same or different is a hydride, substituted or unsubstituted, linear, cyclic or branched, hydrocarbyl having from 1 to 30 carbon atoms, halogen, alkoxides, aryloxides, amides, phosphides, or any other univalent anionic ligand or combination thereof; also, two Q's together may form an alkylidene ligand or cyclometallated hydrocarbyl ligand or other divalent anionic chelating ligand, where g is an integer corresponding to the formal oxidation state of M, and d is an integer selected from 0, 1, 2, 3 or 4 and denoting the degree of substitution, x is an integer from 1 to 4.

In one embodiment, the cyclic bridged bulky ligand metallocene-type catalyst compounds are those where the R substituents on the bulky ligands $L^A$, $L^B$, $(C_5H_{4-d}R_d)$ of formulas (I) and (II) are substituted with the same or different number of substituents on each of the bulky ligands. In another embodiment, the bulky ligands $L^A$, $L^B$, $(C_5H_{4-d}R_d)$ of formulas (I) and (II) are different from each other.

In a preferred embodiment, the bulky ligands of the metallocene-type catalyst compounds of formula (I) and (II) are asymmetrically substituted. In another preferred embodiment, at least one of the bulky ligands $L^A$, $L^B$, $(C_5H_{4-d}R_d)$ of formulas (I) and (II) is unsubstituted.

In the most preferred embodiment, the cyclic bridged metallocene-type catalyst compounds of the invention are achiral.

Other bulky ligand metallocene-type catalysts compounds useful in the invention include cyclic bridged heteroatom, mono-bulky ligand metallocene-type compounds. These types of catalysts and catalyst systems are described in, for example, PCT publication WO 92/00333, WO 94/07928, WO 91/ 04257, WO 94/03506, WO 96/00244 and WO 97/15602 and U.S. Pat. Nos. 5,057,475, 5,096,867, 5,055, 438, 5,198,401, 5,227,440 and 5,264,405 and European publication EP-A-0 420 436, all of which are herein fully incorporated by reference. Other bulky ligand metallocene-type catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398 and 5,753,578 and PCT publications WO 93/08221, WO 93/08199, WO 95/07140, WO 98/11144 and European publications EP-A-0 578 838, EP-A-0 638 595, EP-B-0 513 380, EP-A1-0 816 372, EP-A2-0 839 834 and EP-B1-0 632 819, all of which are herein fully incorporated by reference.

In another embodiment, the cyclic bridged bulky ligand metallocene-type catalyst compound is represented by the formula:

$$L^CAJMQ_n \qquad (III)$$

where M is a Group 3 to 10 metal atom or a metal selected from the Group of actinides and lanthanides of the Periodic Table of Elements, preferably M is a Group 4 to 10 transition metal, and more preferably M is a Group 4, 5 or 6 transition metal, and most preferably M is a Group 4 transition metal in any oxidation state, especially titanium; $L^C$ is a substituted or unsubstituted bulky ligand bonded to M; J is bonded to M; A is bonded to L and J; J is a heteroatom ancillary ligand; and A is a cyclic bridging group; Q is a univalent anionic ligand; and n is the integer 0,1 or 2. In formula (III) above, $L^C$, A and J form a fused ring system. In an embodiment, $L^C$ of formula (III) is as defined above for $L^A$ in formula (I), and A, M and Q of formula (III) are as defined above in formula (I).

In another embodiment of this invention the bulky ligand metallocene-type catalyst compound useful in the invention is represented by the formula:

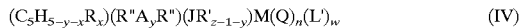
$$(C_5H_{5-y-x}R_x)(R''A_yR'')(JR'_{z-1-y})M(Q)_n(L')_w \qquad (IV)$$

where M is a transition metal from Group 4 in any oxidation state, preferably, titanium, zirconium or hafnium, most preferably titanium in either a +2, +3 or +4 oxidation state. A combination of compounds represented by formula (IV) with the transition metal in different oxidation states is also contemplated. $L^C$ is represented by $(C_5H_{5-y-x}R_x)$ and is a bulky ligand as described above. For purposes of formula (IV) $R_O$ means no substituent. More particularly $(C_5H_{5-y-x}R_x)$ is a cyclopentadienyl ring or cyclopentadienyl-type ring or ring system which is substituted with from 0 to 4 substituent groups R, and "x" is 0, 1, 2, 3 or 4 denoting the degree of substitution. Each R is, independently, a radical selected from a group consisting of 1 to 30 non-hydrogen atoms. More particularly, R is a hydrocarbyl radical or a substituted hydrocarbyl radical having from 1 to 30 carbon atoms, or a hydrocarbyl-substituted metalloid radical where the metalloid is a Group 14 or 15 element, preferably silicon or nitrogen or a combination thereof, and halogen radicals and mixtures thereof. Substituent R groups also include silyl, germyl, amine, and hydrocarbyloxy groups and mixtures thereof. Also, in another embodiment, $(C_5H_{5-y-x}R_x)$ is a cyclopentadienyl ligand in which two R groups, preferably two adjacent R groups are joined to form a ring or ring system having from 3 to 50 atoms, preferably from 3 to 30 carbon atoms. This ring system may form a saturated or unsaturated polycyclic cyclopentadienyl-type ligand such as those bulky ligands described above, for example, indenyl, tetrahydroindenyl, fluorenyl or octahydrofluorenyl.

The $(JR'_{z-1-y})$ of formula (IV) is a heteroatom containing ligand in which J is an element with a coordination number of three from Group 15 or an element with a coordination number of two from Group 16 of the Periodic Table of Elements. Preferably J is a nitrogen, phosphorus, oxygen or sulfur atom with nitrogen being most preferred. Each R' is, independently, a radical selected from the group consisting of hydrocarbyl radicals having from 1 to 20 carbon atoms, or as defined for R in formula (I) above; the "y" is 1 to 4, preferably 1 to 2, most preferably y is 1, and the "z" is the coordination number of the element J. In one embodiment, in formula (IV), the J of formula (III) is represented by $(JR'_{z-1-y})$.

In formula (IV) each Q is, independently, any univalent anionic ligand such as halogen, hydride, or substituted or unsubstituted hydrocarbyl having from 1 to 30 carbon atoms, alkoxide, aryloxide, sulfide, silyl, amide or phosphide. Q may also include hydrocarbyl groups having ethylenic unsaturation thereby forming a $\eta^3$ bond to M. Also, two Q's may be an alkylidene, a cyclometallated hydrocarbyl or any other divalent anionic chelating ligand. The integer n may be 0, 1, 2 or 3.

The $(R''A_yR'')$ of formula (IV) is a cyclic bridging group where A is a Group 13 to 16 element, preferably a Group 14 and 15 element, most preferably a Group 14 element. Non-limiting examples of A include one or more of, or a combination of carbon, silicon, germanium, boron, nitrogen, phosphorous, preferably at least one silicon atom. The two R'''s for a ring or ring system about A, the two R'''s together having from 3 to 100 non-hydrogen atoms, preferably from 3 to 50 carbon atom.

Optionally associated with formula (IV) is L', a Lewis base such as diethylether, tetraethylammonium chloride, tetrahydrofuran, dimethylaniline, aniline, trimethylphosphine, n-butylamine, and the like; and w is a number from 0 to 3. Additionally, L' may be bonded to any of R, R' or Q and n is 0, 1, 2 or 3.

Activator and Activation Methods for the Bulky Ligand Metallocene-Type Catalyst Compounds The above described cyclic bridged bulky ligand metallocene-type catalyst compounds are typically activated in various ways to yield catalyst compounds having a vacant coordination site that will coordinate, insert, and polymerize olefin(s).

For the purposes of this patent specification and appended claims, the term "activator" is defined to be any compound or component or method which can activate any of the bulky ligand metallocene-type catalyst compounds of the invention as described above. Non-limiting activators, for example may include a Lewis acid or a non-coordinating ionic activator or ionizing activator or any other compound including Lewis bases, aluminum alkyls, conventional-type cocatalysts and combinations thereof that can convert a neutral bulky ligand metallocene-type catalyst compound to a catalytically active bulky ligand metallocene cation. It is within the scope of this invention to use alumoxane or modified alumoxane as an activator, and/or to also use ionizing activators, neutral or ionic, such as tri (n-butyl) ammonium tetrakis (pentafluorophenyl) boron or a trisperfluorophenyl boron metalloid precursor or a trisperfluoronaphtyl boron metalloid precursor that would ionize the neutral bulky ligand metallocene-type catalyst compound.

In one embodiment, an activation method using ionizing ionic compounds not containing an active proton but capable of producing both a bulky ligand metallocene-type catalyst cation and a non-coordinating anion are also contemplated, and are described in EP-A- 0 426 637, EP-A-0 573 403 and U.S. Pat. No. 5,387,568, which are all herein incorporated by reference.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451 5,744,656 and European publications EP-A-0 561 476, EP-B1-0 279 586 and EP-A-0 594-218, and PCT publication WO 94/10180, all of which are herein fully incorporated by reference.

Ionizing compounds may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Other activators include those described in PCT publication WO 98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153,157 and 5,453,410 all of which are herein fully incorporated by reference. WO 98/09996 incorporated herein by reference describes activating bulky ligand metallocene-type catalyst compounds with perchlorates, periodates and iodates including their hydrates. WO 98/30602 and WO 98/30603 incorporated by reference describe the use of lithium (2,2'-bisphenyl-ditrimethylsilicate)•94THF as an activator for a bulky ligand metallocene-type catalyst compound. Also, methods of activation such as using radiation (see EP-B 1-0 615 981 herein incorporated by reference), electro-chemical oxidation, and the like are also contemplated as activating methods for the purposes of rendering the neutral bulky ligand metallocene-type catalyst compound or precursor to a bulky ligand metallocene-type cation capable of polymerizing olefins.

It is further contemplated by the invention that other catalysts can be combined with the cyclic bridged bulky ligand metallocene-type catalyst compounds of the invention. For example, see U.S. Pat. Nos. 4,937,299, 4,935,474, 5,281,679, 5,359,015, 5,470,811, and 5,719,241 all of which are herein fully incorporated herein reference.

In another embodiment of the invention one or more bulky ligand metallocene-type catalyst compounds or catalyst systems may be used in combination with one or more conventional-type catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010 published Aug. 1, 1996, all of which are herein fully incorporated by reference.

Method for Supporting

The above described cyclic bulky ligand metallocene-type catalyst compounds and catalyst systems may be combined with one or more support materials or carriers using one of the support methods well known in the art or as described below. In the preferred embodiment, the method of the invention uses a polymerization catalyst in a supported form. For example, in a most preferred embodiment, a bulky ligand metallocene-type catalyst compound or catalyst system is in a supported form, for example deposited on, bonded to, contacted with, or incorporated within, adsorbed or absorbed in, or on, a support or carrier.

The terms "support" or "carrier" are used interchangeably and are any support material, preferably a porous support material, for example, talc, inorganic oxides and inorganic chlorides. Other carriers include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665) and the like. Also, combinations of these support materials may be used, for example, silica-chromium, silica-alumina, silica-titania and the like.

It is preferred that the carrier, most preferably an inorganic oxide, has a surface area in the range of from about 10 to about 700 $m^2/g$, pore volume in the range of from about 0.1 to about 4.0 cc/g and average particle size in the range of from about 5 to about 500 µm. More preferably, the surface area of the carrier is in the range of from about 50 to about 500 $m^2/g$, pore volume of from about 0.5 to about 3.5 cc/g and average particle size of from about 10 to about 200 µm. Most preferably the surface area of the carrier is in the range is from about 100 to about 400 $m^2/g$, pore volume from about 0.8 to about 3.0 cc/g and average particle size is from about 5 to about 100 µm. The average pore size of the carrier of the invention typically has pore size in the range of from 10 to 1000 Å, preferably 50 to about 500 Å, and most preferably 75 to about 350 Å.

Examples of supporting the bulky ligand metallocene-type catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664 and U.S. Application Ser. No. 271,598 filed Jul. 7, 1994 and 788,736 filed Jan. 23, 1997 and PCT publications WO 95/32995, WO 95/14044, WO 96/06187 and WO 97/02297 all of which are herein fully incorporated by reference.

In one embodiment, the cyclic bridged bulky ligand metallocene-type catalyst compounds of the invention may be deposited on the same or separate supports together with an activator, or the activator may be used in an unsupported form, or may be deposited on a support different from the supported bulky ligand metallocene-type catalyst compounds of the invention, or any combination thereof.

There are various other methods in the art for supporting a polymerization catalyst compound or catalyst system of the invention. For example, the cyclic bridged bulky ligand metallocene-type catalyst compound of the invention may contain a polymer bound ligand as described in U.S. Pat. Nos. 5,473,202 and 5,770,755, which is herein fully incorporated by reference; the bulky ligand metallocene-type catalyst system of the invention may be spray dried as described in U.S. Pat. No. 5,648,310, which is herein fully incorporated by reference; the support used with the cyclic bridged bulky ligand metallocene-type catalyst system of the invention is functionalized as described in European publication EP-A-0 802 203, which is herein fully incorporated by reference, or at least one substituent or leaving group is selected as described in U.S. Pat. No. 5,688,880, which is herein fully incorporated by reference.

In a preferred embodiment, the invention provides for a supported cyclic bridged bulky ligand metallocene-type catalyst system that includes an antistatic agent or surface modifier that is used in the preparation of the supported catalyst system as described in PCT publication WO 96/11960, which is herein fully incorporated by reference. The catalyst systems of the invention can be prepared in the presence of an olefin, for example hexene-1.

A preferred method for producing the supported cyclic bridged bulky ligand metallocene-type catalyst system of the invention is described below and is described in U.S.

application Ser. Nos. 265,533, filed Jun. 24, 1994 and 265,532, filed Jun. 24, 1994 and PCT publications WO 96/00245 and WO 96/00243 both published Jan. 4, 1996, all of which are herein fully incorporated by reference. In this preferred method, the cyclic bridged bulky ligand metallocene-type catalyst compound is slurried in a liquid to form a metallocene solution and a separate solution is formed containing an activator and a liquid. The liquid may be any compatible solvent or other liquid capable of forming a solution or the like with the cyclic bridged bulky ligand metallocene-type catalyst compounds and/or activator of the invention. In the most preferred embodiment the liquid is a cyclic aliphatic or aromatic hydrocarbon, most preferably toluene. The cyclic bridged bulky ligand metallocene-type catalyst compound and activator solutions are mixed together and added to a porous support or the porous support is added to the solutions such that the total volume of the bulky ligand metallocene-type catalyst compound solution and the activator solution or the bulky ligand metallocene-type catalyst compound and activator solution is less than four times the pore volume of the porous support, more preferably less than three times, even more preferably less than two times; preferred ranges being from 1.1 times to 3.5 times range and most preferably in the 1.2 to 3 times range.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

The mole ratio of the metal of the activator component to the metal of the supported cyclic bridged bulky ligand metallocene-type catalyst compounds are in the range of between 0.3:1 to 1000:1, preferably 20:1 to 800:1, and most preferably 50:1 to 500:1. Where the activator is an ionizing activator such as those based on the anion tetrakis (pentafluorophenyl)boron, the mole ratio of the metal of the activator component to the metal component of the cyclic bridged bulky ligand metallocene-type catalyst is preferably in the range of between 0.3:1 to 3:1. Where an unsupported cyclic bridged bulky ligand metallocene-type catalyst system is utilized, the mole ratio of the metal of the activator component to the metal of the cyclic bridged bulky ligand metallocene-type catalyst compound is in the range of between 0.3:1 to 10,000:1, preferably 100:1 to 5000:1, and most preferably 500:1 to 2000:1.

In one embodiment of the invention, olefin(s), preferably $C_2$ to $C_{30}$ olefin(s) or alpha-olefin(s), preferably ethylene or propylene or combinations thereof are prepolymerized in the presence of the cyclic bridged bulky ligand metallocene-type catalyst system of the invention prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578 and European publication EP-B-0279 863 and PCT Publication WO 97/44371 all of which are herein fully incorporated by reference.

In one embodiment the polymerization catalyst is used in an unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed to a reactor as described in PCT publication WO 97/46599, which is fully incorporated herein by reference.

In one embodiment, the cyclic bridged metallocene-type catalysts of the invention can be combined with a carboxylic acid salt of a metal ester, for example aluminum carboxylates such as aluminum mono, di- and tri- stearates, aluminum octoates, oleates and cyclohexylbutyrates, as described in U.S. application Ser. No. 09/113,216, filed Jul. 10, 1998.

Polymerization Process

The catalysts and catalyst systems of the invention described above are suitable for use in any polymerization process over a wide range of temperatures and pressures. The temperatures may be in the range of from –60 ° C. to about 280° C., preferably from 50° C. to about 200° C., and the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefins at least one of which is ethylene or propylene.

In one embodiment, the process of this invention is directed toward a solution, high pressure, slurry or gas phase polymerization process of one or more olefin monomers having from 2 to 30 carbon atoms, preferably 2 to 2 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene-type catalysts as described in U.S. Pat. Nos. 5,296,434 and 5,278,264, both of which are herein incorporated by reference.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference).

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include those described in U.S. Pat. Nos. 5,627,242, 5,665,818 and 5,677,375, and European publications EP-A- 0 794 200, EP-A-0 802 202 and EP-B- 634 421 all of which are herein fully incorporated by reference.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555, which are fully incorporated herein by reference A preferred process of the invention is where the process, preferably a slurry or gas phase process is operated in the presence of a bulky ligand metallocene-type catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352 and 5,763,543, which are herein fully incorporated by reference. In another preferred embodiment of the process of the invention, the process is operated by introducing a benzil compound into the reactor and/or contacting a benzil compound with the bulky ligand metallocene-type catalyst system of the invention prior to its introduction into the reactor.

Polymer Product of the Invention

The polymers produced by the process of the invention can be used in a wide variety of products and end-use applications. The polymers produced by the process of the invention include linear low density polyethylene, elastomers, plastomers, high density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc to about 0.930 g/cc. The melt strength of the polymers produced using the catalyst of the invention are greater than 4 cN, preferably greater than 5 cN. For purposes of this patent application and appended claims melt strength is measured with an Instron capillary rheometer in conjunction with the Goettfert Rheotens melt strength apparatus. A polymer melt strand extruded from the capillary die is gripped between two counter-rotating wheels on the apparatus. The take-up speed is increased at a constant acceleration of 24 mm/sec$^2$, which is controlled by the Acceleration Programmer (Model 45917, at a setting of 12). The maximum pulling force (in the unit of cN) achieved before the strand breaks or starts to show draw-resonance is determined as the melt strength.

The temperature of the rheometer is set at 190° C. The capillary die has a length of one inch (2.54 cm) and a diameter of 0.06"(0.15 cm). The polymer melt is extruded from the die at a speed of 3 inch/min (7.62 cm/min). The distance between the die exit and the wheel contact point should be 3.94 inches (100 mm).

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.5 to less than about 8, and most preferably from 3.0 to 8.

In one preferred embodiment, the polymers of the present invention have a $M_z/M_w$, of greater than or equal to 3, preferably greater than 3. $M_z$ is the z-average molecular weight. In another preferred embodiment, the polymers of the invention have a $M_z/M_w$ of greater than or equal to 3.0 to about 4. In yet another preferred embodiment, the $M_z/M_w$ is in the range greater than 3 to less than 4.

Also, the polymers of the invention typically have a narrow composition distribution as measured by Composition Distribution Breadth Index (CDBI). Further details of determining the CDBI of a copolymer are known to those skilled in the art. See, for example, PCT Pat. Application WO 93/03093, published Feb. 18, 1993, which is fully incorporated herein by reference. The bulky ligand metallocene-type catalyzed polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, polymers produced using a bulky ligand metallocene-type catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$)($I_{21}$ is measured by ASTM-D-1238-F) of from 30 to less than 200, more preferably from about 35 to less than 100, and most preferably from 40 to 95.

The polymers of the invention in a preferred embodiment have a melt index ratio ($I_{21}/I_2$)($I_{21}$ is measured by ASTM-D-1238-F) of from preferably greater than 30, more preferably greater than 35, even more preferably greater that 40, still even more preferably greater than 50 and most preferably greater than 65.

The polymers of the invention may be blended and/or coextruded with any other polymer. Non-limiting examples of other polymers include linear low density polyethylenes produced via conventional Ziegler-Natta and/or bulky ligand metallocene-type catalysis, elastomers, plastomers, high pressure low density polyethylene, high density polyethylenes, polypropylenes and the like. Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages thereof, the following examples are offered.

For the following examples, the following was utilized. In all the Examples below the methylalumoxane (MAO) used was a 30 weight percent MAO solution in toluene (typically 13.5 wt % Aluminum and 28.2 wt % MAO by NMR) available from Albemarle Corporation, Baton Rouge, La., the Davison 948 silica dehydrated to 600° C. (silica gel) available from W.R. Grace, Davison Chemical Division, Baltimore, Md. Toluene was anhydrous from Aldrich, and used without further purification. The compounds ($C_3H_6$)$SiCl_2$ and ($C_4H_8$)$SiCl_2$ were purchased from Gelest and Lancaster.

The synthesis of the metallocene compounds of the invention are well known. Example 1 illustrates the typical synthesis route to producing the compounds of the invention including those used in the following examples.

Example 1

Synthesis of ($C_3H_6$)Si($C_5Me_4$)$_2$ZrCl$_2$

To a slurry of $C_5Me_4HLi$ (5.2 g, 40.6 mmol) in THF (100 ml) was added ($C_3H_6$)$SiCl_2$ (2.84 g, 20.3 mmol). The reaction mixture was stirred for 1h and reacted with 1 equivalent NaCp (sodium cylopentadiene)(2.0 M, THF). After stirring for one hour the volatiles were removed and the reaction extracted with pentane and filtered through a glass frit. The filtrate was treated with 2.1 equiv. nBuLi (10.0 M, hexanes), based on ($C_3H_6$)$SiCl_2$ and stirred for 2 h. The volatiles were removed in vacuo and the crude white dianion washed with pentane and collected on a glass frit. One half of the dianion was dissolved in $Et_2O$ (80 ml) and reacted with solid ZrCl4 (2.2 g, 9.4 mmol). The volatiles were removed in vacuo from the greenish reaction mixture and the remaining solid extracted with $CH_2Cl_2$ (60 ml). The extract's volatiles were slowly removed to induce precipitation of the product. A yellow solid was filtered from the solution (1.82 g, 41.0% yield).

Example 2

Catalyst Preparation for ($C_3H_6$)Si($C_5Me_4$)$_2$ZrCl$_2$ ($C_3H_6$)Si($C_5Me_4$)$_2$ZrCl$_2$ (0.63 g, 1.33 mmol) was weighed into a beaker and reacted with 32.0 g 30% MAO in toluene (available from Albemarle Corporation, Baton Rouge, La.) and 32.0 g toluene and stirred until dissolution (10 min). To the reaction mixture was added 24.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant.

Example 3

Catalyst Preparation
Catalyst Preparation for $(C_3H_6)Si(2\text{-methyl}C_9H_5)ZrCl_2$ $(C_3H_6)Si(2\text{-methyl}C_9H_5)(C_5Me_4)ZrCl_2$ (0.40 g, 0.83 mmol) was weighed into a beaker and reacted with 53.5 g 30% MAO in toluene (available from Albemarle Corporation, Baton Rouge, La.) and 53.5 g toluene and stirred until dissolution (10 min). To the reaction mixture was added 40.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant. After drying this catalyst, it was dry-coated with 1.4 g Al Stearate which had been dried in vacuo at 85° C. for 18 hr.

Example 4

Catalyst Preparation for $(C_3H_6)Si(C_5H_4)(C_5Me_4)ZrCl_2$ $(C_3H_6)Si(2\text{-methyl}C_9H_5)(C_5Me_4)ZrCl_2$ (0.39 g, 0.93 mmol) was weighed into a beaker and reacted with 53.5 g 30% MAO in toluene (available from Albemarle Corporation, Baton Rouge, La.) and 53.5 g toluene and stirred until dissolution (10 min). To the reaction mixture was added 40.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant.

Example 5

Catalyst Preparation for $(C_3H_6)Si(C_5Me_4)(3MeC_5H_3)ZrCl_2$ $(C_3H_6)Si(C_5Me_4)(3MeC_5H_3)ZSC_2$ (0.71 g, 1.65 mmol) was weighed into a beaker and reacted with 53.5 g 30% MAO in toluene (available from Albemarle Corporation, Baton Rouge, La.) and 53.5 g toluene and stirred until dissolution (10 min). To the reaction mixture was added 40.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant.

Example 6

Catalyst Preparation for $(C_4H_8)Si(C_5Me_4)(C_5H_4)ZrCl_2$ $(C_4H_8)Si(C_5Me_4)(C_5H_4)ZrCl_2$ (0.71 g, 1.65 mmol) was weighed into a beaker and reacted with 53.5 g 30% MAO in toluene (available from Albemarle Corporation, Baton Rouge, La.) and 53.5 g toluene and stirred until dissolution (10 min). To the reaction mixture was added 40.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant.

Example 7

Catalyst Preparation for 50/50 racemic/meso of $(C_3H_6)Si(2\text{-methyl}C_9H_5)ZrCl_2$ A 50/50 rac-/meso mixture of $(C_3H_6)Si(2\text{-methyl}C_9H_5)_2ZrCl_2$ (0.81 g, 1.65 mmol) was weighed into a beaker and reacted with 53.5 g 30% MAO in toluene (available from Albemarle Corporation, Baton Rouge, La.) and 53.5 g toluene and stirred until dissolution (10 min). To the reaction mixture was added 40.0 g silica gel (Davison 948, 600° C., available from W.R. Grace, Davison Chemical Division, Baltimore, Md.,) and mixed with a spatula. The resulting mud was dried in vacuo at room temperature for 15 h and transferred into a bomb for screening in a continuous gas phase pilot plant.

Example 8

Catalyst Preparation for $(C_3H_6)Si(C_5Me_4(C_5Me_3)ZrCl_2$ $(C_3H_6)Si(C_5Me_4)(C_5Me_3)ZrCl_2$ (0.48 g, 1.05 mmol) was weighed into a beaker and reacted with 33.5 g 30% MAO in toluene (available from Albemarle Corporation, Baton Rouge, La.) and 33.5 g toluene and stirred until dissolution (10 min). To the reaction mixture was added 25.0 g silica gel (Davison 948, 600° C., available from W.R. Grace, Davison Chemical Division, Baltimore, Md.,) and mixed with a spatula. The resulting mud was dried in vacuo at room temperature for 15 b and transferred into a bomb for screening in a continuous gas phase pilot plant.

Example 9

Polymerization for Examples 2 through 8

All the catalysts prepared in Examples 2 through 8 were screened in a fluidized bed reactor equipped with devices for temperature control, catalyst feeding or injection equipment, GC analyzer for monitoring and controlling monomer and gas feeds and equipment for polymer sampling and collecting. The reactor consists of a 6 inch (15.24 cm) diameter bed section increasing to 10 inches (25.4 cm) at the reactor top. Gas comes in through a perforated distributor plate allowing fluidization of the bed contents and polymer sample is discharged at the reactor top.

TABLE 1

| Example | Example 2 | Example 3 | Example 4 | Example 5 | Example 6 | Example 7 | Example 8 |
| --- | --- | --- | --- | --- | --- | --- | --- |
| Temperature (° F.) (° C.) | 170 (76.7) | 175 (79.4) | 175 (79.4) | 175 (79.4) | 175 (79.4) | 175 (79.4) | 175 (79.4) |
| Pressure (psi) (kPa) | 300 (2067) | 300 (2067) | 300 (2067) | 300 (2067) | 300 (2067) | 300 (2067) | 300 (2067) |
| Ethylene (mole %) | 30.4 | 35.2 | 35 | 35.2 | 35.1 | 35 | 35 |
| Hydrogen (mole ppm) | 498 | 816 | 1024 | 812 | 904 | 971 | 686 |
| Hydrogen/Ethylene Concentration ratio | 16.4 | 23.2 | 29.3 | 23.1 | 25.7 | 27.8 | 19.6 |
| Hexene (mole %) | 0.57 | 0.29 | 0.33 | 0.52 | 0.63 | 0.23 | 0.24 |
| Hexene/Ethylene Concentration | 0.019 | 0.008 | 0.009 | 0.015 | 0.018 | 0.007 | 0.01 |
| Bed Weight (g) | 642 | 1773 | 1874 | 1948 | 1868 | 1757 | 1918 |
| Residence Time (hrs) | 3.4 | 4.8 | 2.6 | 4.5 | 8.1 | 4.9 | 4.4 |
| Productivity[1] (g/g) | 1617 | 1493 | 959 | 1406 | 444 | 416 | 1297 |
| Gas Velocity (ft/sec) (cm/sec) | 0.547 (16.7) | 1.54 (47) | 1.6 (49) | 1.49 (45.4) | 1.6 (49) | 1.6 (49) | 1.59 (48.5) |

TABLE 1-continued

| Example | Example 2 | Example 3 | Example 4 | Example 5 | Example 6 | Example 7 | Example 8 |
|---|---|---|---|---|---|---|---|
| Production Rate (g/hr) | 188 | 370 | 713 | 437 | 231 | 416 | 440 |
| Bulk Density (g/cc) | 0.4168 | 0.4748 | 0.4798 | Not Meas. | Not Meas. | 0.4748 | 0.4503 |

[1]Productivity is number of grams of product per gram of catalyst.

Example 10
Catalyst preparation for $(C_3H_6)Si(2\text{-methyl}C_9H_5)(C_5Me_4)ZrCl_2$ 1341 ml of 30% MAO in toluene (available from Albemarle Corporation, Baton Rouge, La.) was added to a 2 gallon glass reactor vessel with a heating/cooling jacket and a helical ribbon blender having a central auger-type shaft. 2200 ml toluene was added to the reaction vessel. A suspension of 22.0 g $(C_3H_6)Si(2\text{-methyl}C_9H_5)(C_5Me_4)ZrCl_2$ in 250 ml toluene was transferred to the reaction vessel via cannula. An additional 150 ml toluene was used to rinse the bottle containing the metallocene compound suspension. The reaction mixture was heated to 155° F. (68.3° C.) and stirred for 1 hr. The reaction mixture was transferred to a large glass flask and 500 g silica gel was added with mixing. Two additional increments of silica gel (250 g each) were added to the mixture. The supported catalyst was added back to the original reactor vessel with stirring and 28.6 g AS-990 in 286 ml of toluene was added. (AS-990 is (N,N-bis(2-hydroxylethyl)octadecylamine $(C_{18}H_{37}N(CH_2CH_2OH)_2)$) available as Kemamine AS-990 from ICI Specialties, Wilmington, Del.). The catalyst was dried by $N_2$ purge at 120° F. (49 ° C.) until free flowing. The dried catalyst was dry-mixed with 3.0 wt % of Aluminum Stearate #22 in a dry box, (AlSt #22 is $(CH_3(CH_2)_{16}COO)_2Al$—OH and is available from Witco Corporation, Memphis, Tenn.), then transferred to a catalyst bomb for testing.

Example 11
Catalyst Preparation for $(C_3H_6)Si(C_5H_4)(C_5Me_4)ZrF_2$ 1609 ml of 30% MAO in toluene (available from Albemarle Corporation, Baton Rouge, La.) was added to a 2 gallon glass reactor vessel with a heating/cooling jacket and a helical ribbon blender having a central auger-type shaft. 2200 ml toluene was added to the reaction vessel. A suspension of 19.4 g $(C_3H_6)Si(C_5H_4)(C_5Me_4)ZrF_2$ in 250 ml toluene was transferred to the reaction vessel via cannula. An additional 200 ml toluene was used to rinse the bottle containing the metallocene compound suspension. The reaction mixture was heated to 155° F. (68.3° C.) and stirred for 1 hr. The reaction mixture was transferred to a large glass flask and 500 g silica gel was added with mixing. Two additional increments of silica gel (250 g each) were added to the mixture. The supported catalyst was added back to the original reactor vessel with stirring and 30.2 g AS-990 in 286 ml of toluene was added. (AS-990 is (N,N-bis(2-hydroxylethyl)octadecylamine $(C_{18}H_{37}N(CH_2CH_2OH)_2)$) available as Kemamine AS-990 from ICI Specialties, Wilmington, Del.). The catalyst was dried by $N_2$ purge at 120° F. (49 ° C.) until free flowing. The dried catalyst was dry-mixed with 2.5 wt % of Aluminum Stearate #22 in a dry box, (AlSt #22 is $(CH_3(CH_2)_{16}COO)_2Al$—OH and is available from Witco Corporation, Memphis, Tenn.), then transferred to a catalyst bomb for testing.

Example 12
Catalyst Preparation for $(C_4H_8)Si(C_5Me_4)(C_5H_4)ZrCl_2$ 1609 ml of 30% MAO in toluene (available from Albemarle Corporation, Baton Rouge, La.) was added to a 2 gallon glass reactor vessel with a heating/cooling jacket and a helical ribbon blender having a central auger-type shaft. 2200 ml toluene was added to the reaction vessel. A suspension of 22.04 g $(C_4H_8)Si(C_5Me_4)(C_5H_4)ZrCl_2$ in 250 ml toluene was transferred to the reaction vessel via cannula. An additional 200 ml toluene was used to rinse the bottle containing the metallocene compound suspension. The reaction mixture was heated to 155° F. (68.3° C.) and stirred for 1 hr. The reaction mixture was transferred to a large glass flask and 500 g silica gel was added with mixing. Two additional increments of silica gel (250 g each) were added to the mixture. The supported catalyst was added back to the original reactor vessel with stirring and 30.2 g AS-990 in 286 ml of toluene was added. (AS-990 is (N,N-bis(2-hydroxylethyl)octadecylamine $(C_{18}H_{37}N(CH_2CH_2OH)_2)$) available as Kemamine AS-990 from ICI Specialties, Wilmington, Del.). The catalyst was dried by $N_2$ purge at 120° F. (49 ° C.) until free flowing. The dried catalyst was dry-mixed with 2.5 wt % of Aluminum Stearate #22 in a dry box, (AlSt #22 is $(CH_3(CH_2)_{16}COO)_2Al$—OH and is available from Witco Corporation, Memphis, Tenn.), then transferred to a catalyst bomb for testing.

Example 14
Polymerizations for Examples 10 through 13

The catalyst systems of the Examples above were then tested in a continuous gas phase fluidized bed reactor which comprised a nominal 18 inch (45.7 cm), schedule 60 reactor having an internal diameter of 16.5 inches (41.9 cm). The fluidized bed is made up of polymer granules. The gaseous feed streams of ethylene and hydrogen together with liquid comonomer were mixed together in a mixing tee arrangement and introduced below the reactor bed into the recycle gas line. Hexene-1 was used as the comonomer. The individual flow rates of ethylene, hydrogen and comonomer were controlled to maintain fixed composition targets. The ethylene concentration was controlled to maintain a constant ethylene partial pressure. The hydrogen was controlled to maintain a constant hydrogen to ethylene mole ratio. The concentration of all the gases were measured by an on-line gas chromatograph to ensure relatively constant composition in the recycle gas stream. The catalyst system was injected directly into the fluidized bed using purified nitrogen as a carrier. Its rate was adjusted to maintain a constant production rate. The reacting bed of growing polymer particles is maintained in a fluidized state by the continuous flow of the make up feed and recycle gas through the reaction zone. A superficial gas velocity of 1–3 ft/sec (31–91 cm/sec) was used to achieve this. The reactor was operated at a total pressure of 300 psig (2069 kPa). To maintain a constant reactor temperature, the temperature of the recycle gas is continuously adjusted up or down to accommodate any changes in the rate of heat generation due to the polymerization. The fluidized bed was maintained at a constant height by withdrawing a portion of the bed at a rate equal to the rate of formation of particulate product. The product is removed semi-continuously via a series of valves into a fixed volume chamber, which is simultaneously vented back to the reactor. This allows for highly efficient removal of the product, while at the same time recycling a large portion of the unreacted gases back to the reactor. This product is purged to remove entrained hydrocarbons and treated with a small steam of humidified nitrogen to deactivate any trace quantities of residual catalyst.

The polymerization conditions for each polymerization utilizing the catalyst systems of the Examples above and results are set forth in Table 1. The catalyst systems of Examples 11 and 13 were run twice as Examples 11A and Example 13A.

Polymer and Film Properties

The polymers and the films produced therefrom of the present invention were produced using the cyclic bridged metallocene-type catalyst systems of the invention. The cyclic bridged metallocene catalyst compounds used were as follows: Catalyst A is cyclotrimethylenesilyl(tetramethyl cyclopentadienyl) (cyclopentadienyl)zirconium dichloride, Catalyst B is cyclotetramethylenesilyl(tetramethyl cyclopentadienyl)(cyclopentadienyl) zirconium dichloride, and Catalyst C is cyclotrimethylenesilyl (tetramethyl cyclopentadienyl)(2-methyl indenyl)zirconium dichloride,

TABLE 2

| VARIABLES | Example 11 | Example 11A | Example 12 | Example 13 | Example 13A |
|---|---|---|---|---|---|
| Temperature (° F.) (° C.) | 185 (85) | 185 (85) | 185 (85) | 185 (85) | 185 (85) |
| Pressure (psi) (kPa) | 300 (2069) | 300 (2069) | 300 (2069) | 300 (2069) | 300 (2069) |
| $C_2$ Partial Pressure (psia) (kPa) | 220.4 (1520) | 220.3 (1520) | 219.5 (1514) | 220.5 (1521) | 220.7 (1522) |
| Ethylene (mole %) | 70 | 70 | 69.8 | 70.1 | 70.1 |
| Hydrogen (mole ppm) | 874.1 | 1628.6 | 1508.3 | 1671.7 | 1429.4 |
| Hydrogen/Ethylene Concentration ratio | 12.48 | 23.3 | 21.6 | 23.86 | 20.38 |
| Hexene (mole %) | 0.77 | 0.81 | 1.43 | 1.68 | 1.73 |
| Hexene/Ethylene Concentration ratio | 0.0111 | 0.0115 | 0.0205 | 0.0240 | 0.0247 |
| Bed Weight (lbs) (Kg) | 297.3 (135) | 296.9 (135) | 272.2 (124) | 294.6 (134) | 270.8 (123) |
| Residence Time (hrs) | 3.39 | 4.39 | 4.61 | 4.55 | 5.24 |
| Gas Velocity (ft/sec) (cm/sec) | 2.25 (68.6) | 2.25 (68.6) | 2.25 (68.6) | 2.25 (68.6) | 2.25 (68.6) |
| Production Rate (lbs/hr) (Kg/Hr) | 88.2 (40) | 67.8 (31) | 59.7 (27) | 64.7 (29) | 52.8 (24) |
| Bulk Density (g/cc) | 0.4658 | 0.4608 | 0.4528 | 0.3879 | 0.4060 |
| Productivity (g/g)[1] | 3613 | 2834 | 2061 | 2428 | 2083 |
| Melt Index (dg/min) ($I_2$) | 0.79 | 1.65 | 0.47 | 1.18 | 0.7 |
| Melt Index Ratio ($I_{21}/I_2$) | 40.7 | 44.4 | 112.6 | 83.1 | 112.58 |
| Density (g/cc) | 0.9223 | 0.9229 | 0.9184 | 0.9216 | 0.9188 |

[1]Productivity is number of grams of product per gram of catalyst

Polymer Data

The properties of the polymer were determined by the following test methods:

| Property | Units | Procedure |
|---|---|---|
| Melt Indices, Melt Flow Ratios | dg/min | ASTM D-1238 |
| Density | g/cc | ASTM D-1505 |
| Haze | % | ASTM D-1003 |
| Gloss @ 45° | % | ASTM D-2457 |
| Tensile @ Yield | mPa | ASTM D-882 |
| Elongation @ Yield | % | ASTM D-882 |
| Tensile @ Break | mPa | ASTM D-882 |
| Elongation @ Break | % | ASTM D-882 |
| 1% Secant Modulus | mPa | ASTM D-882 |
| Dart Drop Impact | g/μm | ASTM D-1709 (A) |
| Elmendorf Tear Resistance | g/μm | ASTM D-1922 |
| Melt Strength | cN | As described in Specification |
| Composition Distribution Breadth Index | % | As described in Specification |

Catalyst D is cyclotrimethylenesilyl(tetramethylcyclopentadienyl)(3-methyl cyclopentadienyl)zirconium dichloride, Catalyst E is cyclotrimethylenesilyl bis(2-methyl indenyl)zirconium dichloride, Catalyst F is cyclotrimethylenesilyl(tetramethyl cyclopentadienyl)(2,3,5-trimethyl cyclopentadienyl)zirconium dichloride; and they all were prepared as described in Example 2. Catalysts A–F were then polymerized similarly as described in Examples 9 and 14 in a gas phase polymerization process producing ethylene/hexene-1 copolymers.

Table 3 includes the data generated using a catalyst of the invention in a gas phase polymerization process similar to that described in Example 14 to produce an ethylene/hexene-1 copolymer. Table 3A below gives film data for the polymers described in Table 3 in Examples 14 through 18.

Table 4 includes the data generated using a catalyst of the invention in a gas phase polymerization process similar to that described in Example 9 to produce an ethylene/hexene-1 copolymer.

TABLE 3

| Example | 14 | 15 | 16 | 17 | 18 | 19 | 20 |
|---|---|---|---|---|---|---|---|
| Catalyst Used | C | C | A | A | B | B | B |
| Density (g/cc) | 0.9196 | 0.9219 | 0.9221 | 0.9175 | 0.9178 | 0.9186 | 0.9250 |
| Melt Index (g/10 min) | 0.90 | 2.06 | 0.74 | 0.86 | 0.92 | 2.16 | 1.27 |

TABLE 3-continued

| Example | 14 | 15 | 16 | 17 | 18 | 19 | 20 |
|---|---|---|---|---|---|---|---|
| Melt Index Ratio ($I_{21}/I_2$) | 36 | 46 | 100 | 77 | 70 | 58 | 68 |
| Melt Strng. (cN) | 6.5 | 4.4 | 6.2 | 5.9 | 4.0 | 4.3 | 4.4 |
| Melting Peaks | | | | | | | |
| $1^{st}$ M.P. (° C.) | 119.5 | 119.7 | 109.70 | 106.2 | 118.7 | 120.03 | 121.20 |
| 2nd. M.P. (° C.) | 108.0 | 107.4 | 120.93 | 117.3 | 104.8 | 110.96 | 110.75 |
| Mn | 23,600 | 15,500 | 20,500 | 23,300 | 23,000 | 19,500 | 23,300 |
| Mw | 128,400 | 127,200 | 104,400 | 124,100 | 116,800 | 91,700 | 117,700 |
| Mz | 401,900 | 449,900 | 335,900 | 400,500 | 414,200 | 308,400 | 407,300 |
| Mw/Mn | 5.4 | 8.2 | 5.1 | 5.3 | 5.1 | 4.7 | 5.1 |
| Mz/Mw | 3.1 | 3.5 | 3.2 | 3.2 | 3.5 | 3.4 | 3.5 |
| CDBI | 75.5 | 69.0 | 73.9 | 78.4 | 62.6 | 57.2 | 76.3 |
| SCB (/1000° C.) | 13.4 | 15.8 | 15.2 | 15.8 | 16.3 | 17.3 | 12.1 |

TABLE 3A

BLOWN FILM PROPERTIES
(2.5 BUR, DIE GAP AND DIE TEMP SETTING VARIED)

| EXAMPLES | | 14A | 15A | 16A | 17A | 18A |
|---|---|---|---|---|---|---|
| Gauge (mil) | | 2.2 | 1.1 | 2.1 | 2.1 | 4.2 |
| 1% SECMOD (psi) | MD | 38100 | 38520 | 36800 | 32150 | 34980 |
| | TD | 45760 | 48030 | 45060 | 39700 | 38800 |
| TNSL@YLD (psi) | MD | 1515 | 1698 | 1550 | 1394 | 1401 |
| | TD | 1748 | 2023 | 1635 | 1519 | 1453 |
| ELNG@YLD (%) | MD | 5.9 | 5.7 | 5.9 | 6.2 | 6.4 |
| | TD | 5.9 | 5.8 | 5.7 | 6.1 | 6.2 |
| TNSL@BRK (psi) | MD | 6268 | 5196 | 4586 | 4863 | 4258 |
| | TD | 6420 | 5286 | 3884 | 4748 | 4276 |
| ELNG@BRK (%) | MD | 594 | 508 | 507 | 543 | 592 |
| | TD | 652 | 615 | 576 | 620 | 650 |
| ELM TEAR (g/mil) | MD | 123 | 40 | 59 | 98 | 182 |
| | TD | 338 | 326 | 347 | 281 | 317 |
| 26" Dart (g/mil) | | 172 | 112 | 98 | 145 | 132 |
| HAZE (%) | | 21.6 | 32.1 | 15.3 | 16.3 | 8.9 |
| GLOSS (%) | | 26 | 18 | 40 | 36 | 62 |

40

TABLE 4

| Example | Catalyst Used | Density (g/cm3) | MI (g/10 min) | MIR (I-21/I-2) | M. S. (cN) | Mn | Mw | Mz | Mw/Mn | Mz/Mw | 1st Tm (° C.) | 2nd. Tm (° C.) | CDBI | SCB (/1000 C.) |
|---|---|---|---|---|---|---|---|---|---|---|---|---|---|---|
| 21 | A | 0.9232 | 1.45 | 76 | 5.5 | 15,200 | 92,100 | 303,500 | 6.1 | 3.3 | 112.8 | 120.8 | 81.7 | 14.9 |
| 22 | A | 0.9211 | 1.58 | 76 | 4.9 | 13,100 | 86,100 | 325,500 | 6.57 | 3.78 | 108.4 | 118.2 | 82.1 | 16.6 |
| 23 | A | 0.9215 | 0.89 | 84 | 8.5 | 19,000 | 104,100 | 358,700 | 5.48 | 3.45 | 105.8 | 120.0 | 80.7 | 16.0 |
| 24 | A | 0.9189 | 0.52 | 119 | 7.0 | 21,900 | 107,500 | 321,200 | 4.91 | 2.99 | 119.9 | 109.0 | 61.2 | 17.5 |
| 25 | A | 0.9122 | 0.38 | 120 | 7.8 | 22,700 | 114,500 | 353,400 | 5.04 | 3.09 | 119.2 | 107.7 | 49.9 | 20.9 |
| 26 | A | 0.9249 | 1.69 | 56 | 5.7 | 24,400 | 96,600 | 329,300 | 3.96 | 3.41 | 113.7 | s | 58.5 | 12.3 |
| 27 | D | 0.9221 | 0.92 | 79 | 5.7 | 5,140 | 118,500 | 433,100 | 23.05 | 3.65 | 117.4 | 103.4 | 74.3 | 17.5 |
| 28 | B | 0.9209 | 0.98 | 95 | 5.8 | 12,300 | 101,400 | 395,500 | 8.24 | 3.90 | 107.3 | 118.1 | 81.7 | 16.2 |
| 29 | B | 0.9126 | 1.51 | 63 | 5.5 | 15,900 | 91,700 | 319,300 | 5.77 | 3.48 | 101.2 | 110.4 | 82.0 | 18.6 |
| 30 | B | 0.9206 | 0.82 | 77 | 7.7 | 20,700 | 112,800 | 383,800 | 5.45 | 3.40 | 107.4 | 119.4 | 82.1 | 15.4 |
| 31 | E | 0.9220 | 1.04 | 44 | 17.3 | 5,570 | 140,500 | 2,072,000 | 25.22 | 14.75 | 121.0 | 104.7 | 58.1 | 17.0 |
| 32 | F | 0.9228 | 0.54 | 174 | — | — | — | — | — | — | — | — | — | — |

While the present invention has been described and illustrated by reference to particular embodiments, those of ordinary skill in the art will appreciate that the invention lends itself to variations not necessarily illustrated herein. For example, it is contemplated that a the cyclic bridged metallocene-type catalyst compound of the invention can be combined with one or more non-cyclic bridged metallocene-type catalyst compounds. It is also contemplated that the process of the invention may be used in a series reactor polymerization process. For example, a supported cyclic bridged bulky ligand metallocene-type catalyst compound is used in one reactor and a non-cyclic bridged or unbridged, bulky ligand metallocene-type catalyst compound being used in another or vice-versa. For this reason, then, reference should be made solely to the appended claims for purposes of determining the true scope of the present invention.

We claim:

1. A gas phase process for polymerizing olefin(s) to produce a polymer product comprising contacting the olefin(s), under polymerization conditions, with a catalyst system comprising an achiral cyclic bridged bulky ligand metallocene catalyst compound and an activator, wherein the polymer product is an ethylene copolymer having a $I_{21}/I_2$ greater than 40.

2. The process of claim 1 wherein the achiral cyclic bridged bulky ligand metallocene catalyst compound has two bulky ligands.

3. The process of claim 2 wherein the bulky ligands are differently substituted.

4. The process of claim 1 wherein the polymer product is an ethylene copolymer having a $M_z/M_w$ greater than or equal to 3.

5. The process of claim 1 wherein the polymer product has $M_z/M_W$ greater than 3 and an $I_{21}/I_2$ of greater than 60.

6. The process of claim 1 wherein the achiral cyclic bridged bulky ligand metallocene catalyst compound is represented by the formula:

$$L^A(R'A_xR')L^BMQ_n \qquad (I)$$

wherein M is a Group 4, 5, 6 transition metal, $L^A$ and $L^B$ is an unsubstituted or substituted, cyclopentadienyl ligand or cyclopentadienyl-type bulky ligand bonded to M; $(R'A_xR')$ is a cyclic bridging group wherein A is one or more of, or a combination of carbon, germanium, silicon or tin bridging $L^A$ and $L^B$, and the two R"s form a cyclic ring or ring system with A; independently, each Q is a monoanionic ligand, or optionally two Q's together form a divalent anionic chelating ligand; and where n is 0, 1 or 2 depending on the formal oxidation state of M, and x is an integer from 1 to 4.

7. The process of claim 6 wherein one of $L^A$ or $L^B$ is a substituted cyclopentadienyl or a substituted cyclopentadienyl-type bulky ligand.

8. The process of claim 1 wherein the catalyst system is supported.

9. A gas phase process for polymerizing ethylene alone or in combination with one or more other olefin(s) comprising contacting the ethylene alone or in combination with one or more olefin(s), under polymerization conditions, with a catalyst system comprising a cyclic bridged bulky ligand metallocene catalyst compound and an activator, the process producing a polymer product having a $M_z/M_w$ greater than or equal to 3 and an $I_{21}/I_2$ of greater than 40.

10. The process of claim 9 wherein the catalyst system further comprises a carrier.

11. The process of claim 9 wherein the polymer product has a $M_z/M_w$ greater than 3, an $I_{21}/I_2$ of greater than 60.

12. The process of claim 9 wherein the process is a continuous gas phase process.

13. The process of claim 9 wherein the polymer product has a $M_z/M_w$ greater than 3 and a $M_w/M_n$ greater than 4.

14. A gas phase process for polymerizing ethylene and at least one alpha-olefin having from 3 to 20 carbon atoms comprising contacting the ethylene and the at least one alpha-olefin having from 3 to 20 carbon atoms, under polymerization conditions, with a catalyst system comprising a cyclic bridged bulky ligand metallocene catalyst compound, an activator and a carrier, the process producing a polymer product having a density greater than 0.900 g/cc, $I_{21}/I_2$ greater than 40, and a $M_z/M_w$ greater than or equal to 3.

15. The process of claim 14 wherein the cyclic bridged bulky ligand metallocene catalyst compound is achiral.

16. The process of claim 14 wherein the cyclic bridged bulky ligand metallocene catalyst compound is represented by the formula:

$$L^A(R'A_xR')L^BMQ_n \qquad (I)$$

wherein M is a Group 4, 5, 6 transition metal, $L^A$ and $L^B$ are bonded to M and are different, $L^A$ and $L^B$ are selected from the group consisting of unsubstituted or substituted, cyclopentadienyl ligands or unsubstituted or substituted, cyclopentadienyl-type bulky ligand; $(R'A_xR')$ is a cyclic bridging group where A is one or more of, or a combination of carbon, germanium, silicon or tin bridging $L^A$ and $L^B$, and the two R"s form a cyclic ring or ring system with A; independently, each Q is a monoanionic ligand, or optionally two Q's together form a divalent anionic chelating ligand; and where n is 0, 1 or 2 depending on the formal oxidation state of M, and x is an integer from 1 to 4.

17. The process of claim 14 wherein the cyclic bridged bulky ligand metallocene catalyst compound is selected from one of the group consisting of cyclotrimethylenesilyl (tetramethyl cyclopentadienyl) (cyclopentadienyl)zirconium dichloride, cyclotetramethylenesilyl (tetramethyl cyclopentadienyl)(cyclopentadienyl)zirconium dichloride, cyclotrimethylenesilyl (tetramethyl cyclopentadienyl)(2-methyl indenyl) zirconium dichloride, cyclotrimethylenesilyl(tetramethyl cyclopentadienyl)(3-methyl cyclopentadienyl) zirconium dichloride, cyclotrimethylenesilyl (tetramethyl cyclopentadienyl)(2,3,5-trimethyl cyclopentadienyl) zirconium dichloride, and cyclotrimethylenesilyl bis(tetra methyl cyclopentadienyl) zirconium dichloride.

18. The process of claim 14 wherein the polymer product has a density greater than 0.910 g/cc, $I_{21}/I_2$ greater than 60, a $M_z/M_w$ greater than 3, and a $M_w/M_n$ greater than 5.

19. The process of claim 16 where x is 1.

20. The process of claim 16 wherein $L^A$ and $L^B$ are substituted or unsubstituted cyclopentadienyl rings.

21. The process of claim 16 wherein a least one of $L^A$ and $L^B$ is a cyclopentadienyl ring.

22. The process of claim 16 wherein $L^A$ is a substituted cyclopentadienyl ring.

23. The process of claim 14 wherein the cyclic bridged bulky ligand metallocene catalyst compound is achiral.

24. The process of claim 14 wherein the $I_{21}/I_2$ is greater than 65 and the $M_z/M_w$ is greater than 3.1 to less than 4.

* * * * *